US011896509B2

(12) United States Patent
Teichman et al.

(10) Patent No.: US 11,896,509 B2
(45) Date of Patent: Feb. 13, 2024

(54) TISSUE ANCHORING DEVICE

(71) Applicant: Endoron Medical Ltd., Kfar Saba (IL)

(72) Inventors: Eyal Teichman, Hod HaSharon (IL); Ron Karmeli, Haifa (IL); Tanhum Feld, Moshav Merhavia (IL)

(73) Assignee: Endoron Medical Ltd., Kfar Saba (IL)

( * ) Notice: Subject to any disclaimer, the term of this patent is extended or adjusted under 35 U.S.C. 154(b) by 0 days.

(21) Appl. No.: 17/744,683

(22) Filed: May 15, 2022

(65) Prior Publication Data
US 2022/0331133 A1  Oct. 20, 2022

Related U.S. Application Data

(63) Continuation of application No. PCT/IL2021/051152, filed on Sep. 22, 2021.

(60) Provisional application No. 63/081,386, filed on Sep. 22, 2020.

(51) Int. Cl.
*A61F 2/848* (2013.01)
*A61F 2/958* (2013.01)
*A61F 2/82* (2013.01)

(52) U.S. Cl.
CPC ........ *A61F 2/958* (2013.01); *A61F 2002/823* (2013.01); *A61F 2220/0016* (2013.01); *A61F 2230/0017* (2013.01)

(58) Field of Classification Search
CPC .. A61F 2/958; A61F 2/07; A61F 2/848; A61F 2002/823; A61F 2002/8486; A61F 2002/8483; A61F 2220/0008; A61F 2220/0016; A61F 2220/0017
See application file for complete search history.

(56) References Cited

U.S. PATENT DOCUMENTS

| 2003/0220683 | A1  | 11/2003 | Minasian et al. | |
|---|---|---|---|---|
| 2009/0048665 | A1* | 2/2009 | Miron | A61B 17/11 623/1.36 |
| 2012/0130470 | A1* | 5/2012 | Agnew | A61F 2/86 623/1.36 |
| 2013/0172983 | A1* | 7/2013 | Clerc | A61F 2/848 623/1.16 |
| 2015/0018933 | A1* | 1/2015 | Yang | A61F 2/07 623/1.14 |
| 2018/0036111 | A1* | 2/2018 | Despalle de Béarn | A61F 2/90 |
| 2018/0116798 | A1* | 5/2018 | Perszyk | A61F 2/2445 |
| 2018/0289476 | A1* | 10/2018 | Vyas | A61F 2/2418 |

FOREIGN PATENT DOCUMENTS

| WO | WO 2019/239409 | 12/2019 |
|---|---|---|
| WO | WO 2022/064492 | 3/2022 |

OTHER PUBLICATIONS

International Search Report and the Written Opinion dated Mar. 1, 2022 From the International Searching Authority Re. Application No. PCT/IL21/51152. (12 Pages).

(Continued)

*Primary Examiner* — Katherine M Rodjom

(57) ABSTRACT

A tissue anchoring device including an expandable frame and at least one anchor having a tissue penetrating portion. The anchor is attached to the expandable frame through a plurality of beams forming a frame or a tab that enable the anchor to elastically bend with respect to a longitudinal axis of the expandable frame.

6 Claims, 19 Drawing Sheets

(56) References Cited

OTHER PUBLICATIONS

Invitation to Pay Additional Fees Dated Dec. 7, 2021 From the International Searching Authority Re. Application No. PCT/IL2021/051152. (2 Pages).
International Preliminary Report on Patentability dated Apr. 6, 2023 From the International Bureau of WIPO Re. Application No. PCT/IL2021/051152. (9 Pages).

* cited by examiner

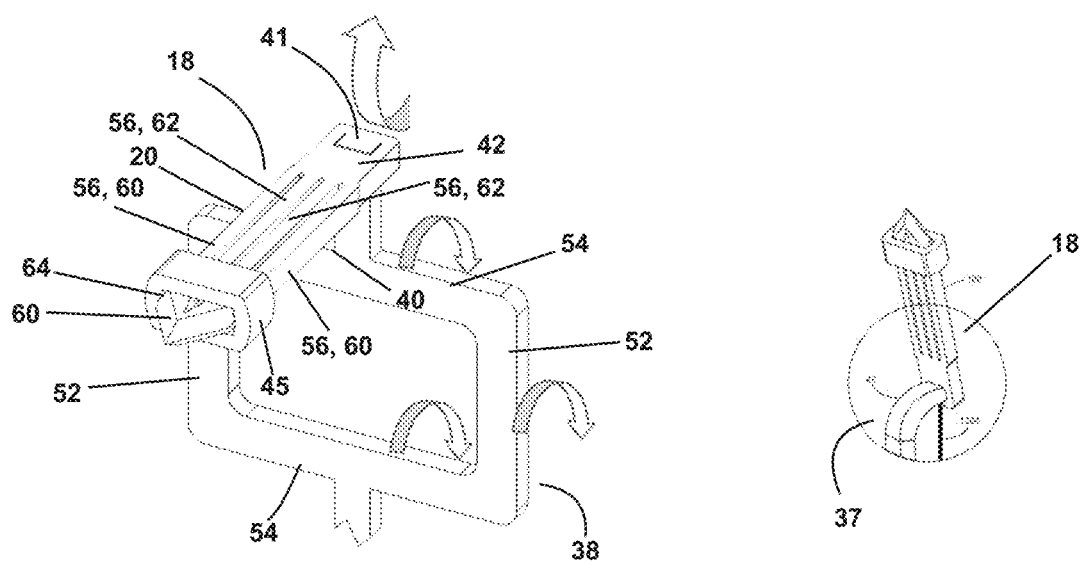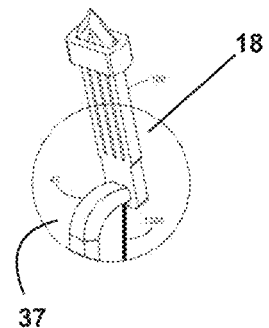
FIG. 5
FIG. 6

TISSUE ANCHORING DEVICE

RELATED APPLICATIONS

This application is a Continuation of PCT Patent Application No. PCT/IL2021/051152 having International filing date of Sep. 22, 2021 which claims the benefit of priority under 35 USC § 119(e) of U.S. Provisional Patent Application No. 63/081,386 filed on Sep. 22, 2020. The contents of the above applications are all incorporated by reference as if fully set forth herein in their entirety.

FIELD AND BACKGROUND OF THE INVENTION

The present invention relates to a tissue anchoring device and to a method and system for using same. Embodiments of the present invention relate to an expandable frame carrying deployable tissue anchors for anchoring an endoluminal device such as a stent graft to tissue.

Vascular aneurysms are characterized by abnormal dilation of a blood vessel that typically results from weakening of the arterial wall caused by disease or genetic predisposition. Aneurysms have been commonly treated by open surgical procedures in which the diseased vessel segment is bypassed or covered with a protective graft.

In more recent years, open procedures have been replaced with minimally invasive procedures that utilize endoluminal stent grafts that enable blood flow through the vessel while bypassing the aneurysm site.

Such stent grafts typically include a metallic support structure carrying a graft material such as Dacron, or polytetrafluoroethylene (PTFE). The graft material is sealed against the vessel wall by the support structure.

Although effective in sealing off the aneurysm, stent grafts can migrate over time due to the force associated with the blood flowing through the stent graft and the expansion and contraction of the arteries due to the pulsation of blood therethrough. Such migration can lead to leakage of blood into the aneurysm site.

Anchors for tissue fixation and stents carrying such anchors have been developed in order to prevent stent graft migration. However, such solutions have not fully addressed the problem of migration due to the limited vessel wall area for fixation above an aneurysm and poor tissue fixation capabilities of such anchors.

There is thus a need for, and it would be highly advantageous to have, a tissue anchoring device that can be used to anchor a stent graft to a vessel wall devoid of the above limitations.

SUMMARY OF THE INVENTION

According to one aspect of the present invention there is provided a tissue anchoring device comprising an expandable frame having a proximal end and a distal end and at least one anchor having a tissue penetrating portion attached to the frame through a plurality of beams forming a frame, the at least one anchor being capable of elastic bending with respect to a longitudinal axis of the expandable frame, the elastic bending being through torsion of a first strut of the plurality of struts and bending of at least a second strut of the struts.

According to embodiments of the present invention the tissue penetrating portion is pointed at an angle with respect to the longitudinal axis of the frame, the angle being selected from a range of 45 to 90 degrees, e.g., 60 degrees.

According to embodiments of the present invention the at least one anchor can be elastically bent from a first direction in which the tissue penetrating portion points at the angle to a second direction in which the tissue penetrating portion is generally pointing parallel to the longitudinal axis of the frame.

According to embodiments of the present invention the at least one anchor includes a restraining element being for restraining the tissue penetrating portion at a first configuration for delivery into a tissue, wherein moving of the restraining element along the at least one anchor releases the tissue penetrating portion to a second configuration for securement to a tissue.

According to embodiments of the present invention the tissue penetrating portion includes two tissue-penetrating prongs.

According to embodiments of the present invention the restraining element maintains the two tissue-penetrating prongs juxtaposed throughout their length when in the configuration for delivery into the tissue.

According to embodiments of the present invention the two tissue-penetrating prongs are elastically deflected away from each other when the restraining element is moved along the anchor.

According to embodiments of the present invention the restraining element is a restraining sleeve.

According to embodiments of the present invention the tissue penetrating portion includes a stop for preventing movement of the restraining sleeve over a tissue penetrating tip of the tissue penetrating portion.

According to another aspect of the present invention there is provided a tissue anchoring device comprising an expandable frame having a proximal end and a distal end and at least one anchor having a tissue penetrating portion attached to the frame, the tissue penetrating portion being pointed at an angle with respect to a longitudinal axis of the frame, the angle being selected from a range of 45-90 degrees.

According to embodiments of the present invention the at least one anchor includes a restraining element being for restraining the tissue penetrating portion at a first configuration for delivery into a tissue, wherein moving of the restraining element along the at least one anchor releases the tissue penetrating portion to a second configuration for securement to a tissue.

According to embodiments of the present invention the tissue penetrating portion includes two tissue-penetrating prongs.

According to embodiments of the present invention the restraining element maintains the two tissue-penetrating prongs juxtaposed throughout their length when in the configuration for delivery into the tissue.

According to embodiments of the present invention the two tissue-penetrating prongs are deflected away from each other when the restraining element is moved along the anchor.

According to embodiments of the present invention the restraining element is a restraining sleeve.

According to embodiments of the present invention the tissue penetrating portion includes a stop for preventing movement of the restraining sleeve over the tip of the tissue penetrating portion.

According to embodiments of the present invention the at least one anchor can be elastically bent from a first direction in which the tissue penetrating portion points at the angle to a second direction in which the tissue penetrating portion is generally pointing parallel to the longitudinal axis of the frame.

According to another aspect of the present invention there is provided a tissue anchoring device comprising an expandable frame having a proximal end and a distal end and at least one anchor having a tissue penetrating portion attached to the frame, the at least one anchor being detachable from the frame following anchoring of the at least one anchor into a tissue.

According to embodiments of the present invention the tissue penetrating portion is pointed at an angle with respect to the longitudinal axis of the frame, the angle being selected from a range of 45-90 degrees.

According to embodiments of the present invention the at least one anchor can be elastically bent from a first direction in which the tissue penetrating portion points at the angle to a second direction in which the tissue penetrating portion is generally pointing parallel to the longitudinal axis of the frame.

According to embodiments of the present invention the at least one anchor is detachable from the frame when pointed at the second direction.

According to embodiments of the present invention the at least one anchor includes a restraining element being for restraining the tissue penetrating portion at a first configuration for delivery into a tissue, wherein moving of the restraining element along the at least one anchor releases the tissue penetrating portion to a second configuration for securement to a tissue.

According to embodiments of the present invention the tissue penetrating portion includes two tissue-penetrating prongs.

According to embodiments of the present invention the restraining element maintains the two tissue-penetrating prongs juxtaposed throughout their length when in the configuration for delivery into the tissue.

According to embodiments of the present invention the two tissue-penetrating prongs are deflected away from each other when the restraining element is moved along the anchor.

According to embodiments of the present invention the restraining element is a restraining sleeve.

According to embodiments of the present invention the tissue penetrating portion includes a stop for preventing movement of the restraining sleeve over a tissue penetrating tip of the tissue penetrating portion.

According to another aspect of the present invention there is provided a method of securing a graft to a tissue comprising: (a) providing a tissue anchoring device including an expandable frame having a proximal end and a distal end and at least one anchor having a tissue penetrating portion attached to the frame; (b) collapsing the expandable frame within delivery catheter such that the at least one anchor is forced in a direction that is generally parallel to a longitudinal axis of the frame; (c) releasing the device within the graft positioned against the tissue thereby releasing the at least one anchor to elastically move to a second direction that is angled towards the graft; (d) inflating a first balloon within the frame to thereby stabilize a portion of the frame against the graft and the tissue; (e) inflating a second balloon within the frame to thereby force the tissue penetrating portion of the at least one anchor through the graft and into the tissue thereby securing the graft to the tissue.

According to embodiments of the present invention the first balloon and the second balloon are attached side-by-side (proximal to distal) to single catheter shaft.

According to embodiments of the present invention the second balloon is positioned within the first balloon.

According to another aspect of the present invention there is provided tissue anchoring system comprising: (a) a device including an expandable frame having a proximal end and a distal end and at least one anchor having a tissue penetrating portion attached to the frame, the tissue penetrating portion being pointed at an angle with respect to a longitudinal axis of the frame, the angle being selected from a range of (−45)-(90) degrees; and (b) a delivery catheter for: (i) maintaining the frame collapsed such with the at least one anchor maintained a direction that is generally parallel to a longitudinal axis of the frame; and (ii) releasing the device to self-expand thereby releasing the at least one anchor to elastically move to a second position that is angled with respect to the longitudinal axis of the frame.

According to embodiments of the present invention the system further comprises a balloon catheter positioned within the delivery catheter.

According to embodiments of the present invention the balloon catheter includes two separately inflatable balloons.

According to another aspect of the present invention there is provided a balloon catheter comprising two separately inflatable balloons attached along a catheter shaft (arranged proximal to distal on the shaft), the balloon catheter including a sheath covering the distal balloon and being attached at distal and proximal necks of the distal balloon, wherein a space between the distal balloon and said sheath (forming a volume when the distal balloon is not inflated) is fluidly accessible via a conduit running through the distal and/or proximal necks.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 5 illustrates torsion and bending of the beams of a frame connecting the tissue anchor to the expandable frame.

FIG. 6 illustrates bending of a tab connecting the tissue anchor to the expandable frame.

DESCRIPTION OF SPECIFIC EMBODIMENTS OF THE INVENTION

Figure 1A:
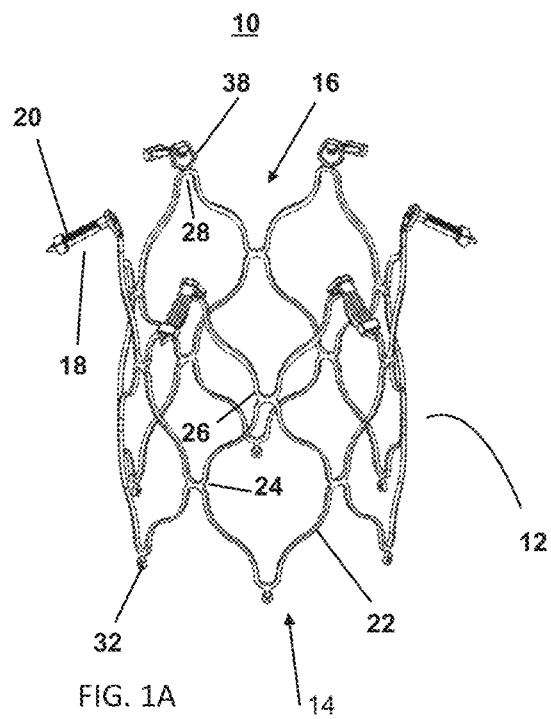
FIGS. 1A-B illustrate an isometric (FIG. 1A) and side (FIG. 1B) views of one embodiment of the present device shown in an expanded configuration.

The present invention is of a tissue anchoring device which can be to anchor an endoluminal device within a blood vessel. Specifically, the present invention can be used to anchor a stent graft used for aneurysm repair to prevent migration and leakage of blood.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In a previously filed patent application (WO2019239409), Applicant has disclosed a graft securing system that includes tissue anchors attached around an expandable frame. While further developing this system, the present inventors have isolated and identified unique features that provide benefits to both device anchoring and delivery.

Thus, according to one aspect of the present invention there is provided a tissue anchoring device that includes an expandable frame having a proximal end and a distal end and at least one anchor (having a tissue penetrating portion) attached to the frame.

The tissue anchoring device of the present invention can be used to anchor any endoluminal device within any biological vessel. Examples include anchoring of grafts or stent grafts within the vasculature, anchoring of valves within the cardio vasculature, blocking of arteries and veins within the vasculature, or anchoring a vasculature bypass.

The expandable frame can be self-expanding, mechanically expanded (e.g., via a balloon) or a combination of both—self-expanding to a first diameter and then mechanically expanded to a final diameter.

The expandable frame can be constructed from an alloy such as Nitinol or stainless steel or from a polymer or a combination of both. The expandable frame can be configured from struts and/or rings and can include any number of each. For example, the expandable frame can be constructed from an open or closed cell layout of struts, torturous (wavy) struts or zig-zagging struts that run the length of the expandable frame from a proximal end to a distal end. The peaks or valleys of such struts can be interconnected or not. In another example, the expandable frame can be constructed from torturous rings interconnected by short linear or torturous struts.

Frame design can be applied to the present expandable frame with crowns, strut and connector structures. Rings provide radial support and expansion capacity whereas connectors hold rings together, contributing to the stent longitudinal structural stability. One of ordinary skill in the art would be capable of identifying numerous expandable frame configurations suitable for use with the present device.

The expandable frame can be constructed by any one of numerous approaches known in the art. For example, by laser cutting or etching of a tube or by laser cutting a Nitinol/stainless steel sheet and rolling and welding it to a final tube shape.

Typical dimensions of the expandable frame can be 10-50 mm in length, 18-38 mm in diameter (expanded) and 3-7 mm in diameter (collapsed). The struts/rings can be 0.1-1 mm in width and 0.1-0.5 mm in thickness.

The tissue anchor carried by the expandable frame can be fabricated along with the expandable frame (e.g., integral to the frame design) or it can be fabricated separately and attached thereto via welding/soldering or a releasable mechanism (e.g., a lock pin released via a connected pull wire).

The present device can include one or more tissue anchors arranged in a specific pattern around and/or along the expandable frame (typically around a circumference close or at the distal end). The tissue anchor includes a base attached to the expandable frame (either directly or through a tab or frame—further described hereinbelow). The anchor body includes a tissue penetrating portion that includes two prongs that are restrained for delivery in a co-linear configuration (juxtaposed along their length) by a restraining element capable of sliding along the anchor body. When slid backward towards the expandable frame the prongs are released and splay out to a tissue anchoring configuration. This restraining element (e.g., sleeve or collar) is pushed backwards when the prongs are driven into graft material and/or tissue such that when the prongs are through the graft/tissue they splay out (deflect away from each other) to anchor against the far side of the graft and/or tissue. Such a configuration provides anchor-graft/tissue fixation by simply driving the anchor through the tissue, i.e., separate activation of an anchor locking mechanism is not required.

The tissue anchor also includes a tissue penetrating tip that is designed with a stop feature that prevents the restraining element from moving beyond the penetrating tip. Such a stop can include a protrusion in the tip that will prevent distal movement of the restraining element along the tip.

The tissue anchors are attached to a tab or frame that is in turn attached to a strut or ring of the expandable frame.

The expandable frame and tissue anchors are fabricated such that the tissue anchors point radially outward from the frame regardless if the frame is expanded or collapsed. When the frame is collapsed for delivery, the tissue anchors deflect inward to a position that is roughly parallel to the longitudinal axis of the expandable frame. The tab or frame enable the anchor to elastically bend from a first direction in which the tissue penetrating portion points at an angle with respect to the longitudinal axis of the expandable frame (i.e., radially outward) to a second direction in which the tissue penetrating portion is generally pointing parallel to the longitudinal axis of the frame.

While reducing the present invention to practice, the present inventors have discovered that a device that includes tissue anchors that are oriented radially outward at an angle that is perpendicular (90 degrees) to the longitudinal axis of the frame is less effective at penetrating the graft due to the fact that the staple to graft wall angle (while the device is deployed with in a graft) largely deviate from the optimal 90 degree angle as result of radial skewing of the frame struts that carry the staple.

In order to traverse this limitation, the present inventors experimented with several tissue anchor angles and have identified that and angle of 45-70 degrees (with respect to the longitudinal axis of the expandable frame and with the tissue penetrating portion pointing downward—in a proximal direction) or 15-50 degrees downward from an axis normal to the expandable frame) provides the best penetration and anchoring results. This is due to the fact that the pre-shaped downward angle of the staple to frame interface element compensates for the frame struts skewing at delivery.

As is mentioned hereinabove, the tissue anchor is attached to the expandable frame through a tab or a support frame. While a tab can provide the elasticity needed for elastically bending the tissue anchor from a tissue penetrating position (pointing radially outward) to a device delivery position (parallel to the longitudinal axis of a collapsed expandable frame), the present inventors have discovered that a tab that is sufficiently elastic might not provide the support necessary for graft/tissue penetration due to its relatively low torsional and bending stiffness.

In order to improve penetration of the anchor into the graft/tissue, while maintaining the ability to pack the device into the delivery system, the present inventors have devised a support frame to attach the tissue anchor to the expandable frame. Such a support frame includes 4-5 beams (square/rectangle or trapezoid, respectively) with 2 beams serving as uprights and two or three beams serving as cross members. During the crimping process (when the anchor is forced from an initial perpendicular orientation to a parallel orientation) the uprights bend while the cross members twist (torsion), this combined bending and twisting facilitates anchor bending through a range of more than 90 degrees while maintaining the stress over the beams within the allowable elasticity range per frame material. (e.g., max. strain 6-7%).

The present device can also be configured such that the expandable frame is only used to deliver the anchors into the graft/tissue. In other words, following anchoring, the tissue anchors can be detached from the expandable frame (detached from the tab or support frame) and the expandable frame can then be collapsed and removed from the body.

Several configurations can be used to provide this functionality. For example, the collapsible frame can form a part of the delivery system with the anchor attached to the frame through a pin locking mechanism that is connected to a pull-wire. Once the expandable frame is positioned and deployed the anchors are forced into the tissue (via, for example, a balloon which is part of the delivery system). The pins can then be released from the tabs holding the anchors to the expandable frame by pulling the pull-wires through the delivery system. The delivery system can then be pulled back to release the anchors from the tabs and the delivery system and expandable frame can then be removed from the body.

The present device can form a part of a tissue anchoring system that also includes a delivery catheter and a deployment catheter (to deploy the tissue anchors into the tissue).

The delivery catheter is used to deliver the device into a biological vessel (e.g., blood vessel), while the deployment catheter is used to stabilize the device in the vessel and drive the tissue anchors through the graft/tissue.

While experimenting the present device in an animal aorta (ex-vivo), the present inventors discovered that pushing the tissue anchors through the graft/tissue using a balloon catheter without a prior step of stabilizing the device resulted in frame migration and penetration failure. This is due to the geometric state of the anchors and the collapsible frame struts during the activation process. Following initial expansion of the expandable frame, most of the frame and the anchor tips contact the graft, while the anchor base is located about 6 mm inward (away from the graft). When a balloon is inflated within the expandable frame in order to push the anchors into the graft and tissue, the struts of the expandable frame create a triangle around the anchor that also applies forces along the graft longitudinal axis. Such geometry and 'side' force can change the angle between the anchor and the graft wall and as result can lead to mis-penetration failure.

In order to maintain device stability throughout anchor delivery, the present inventors have devised a balloon catheter that includes two balloons that can be used to simultaneously stabilize the device within the vessel (against longitudinal movement) and force the tissue anchors into the graft/tissue at an optimal angle. Such a dual balloon can include two side-by-side balloons (along length of catheter) or a short balloon within a long balloon with the short balloon being movable/stationary longitudinally within the long balloon. In either configurations, one balloon can be used to stabilize the device (e.g., proximal balloon in the side-by-side configuration or the outer/inner balloon in the balloon-within-balloon configuration) while the other balloon can be used to force the tissue anchors through the graft/tissue.

Referring now to the drawings, FIGS. 1A-3 illustrate one embodiment of the present device which is referred to as device 10. FIGS. 4-6 illustrate the tissue anchor and tab/frame support of device 10.

Device 10 includes an expandable frame 12 having a proximal end 14 and a distal end 16. Device 10 further includes at least one anchor 18 (6 shown in FIGS. 1A-3) having a tissue penetrating portion 20.

Expandable frame 12 includes struts 22 (12 shown in FIGS. 1A-B) arranged around the circumference of frame 12 and extending from proximal end 14 to distal end 16. In the configuration shown in FIGS. 1A-B, struts 22 follow a meandering path proximal to distal (somewhat sinusoidal) through peaks 24 and valleys 26. Peaks 24 and valleys 26 of adjacent struts 22 are co-attached. Proximal ends 14 and distal ends 16 of each adjacent strut 22 form loops 28. This configuration can also be described as a longitudinal series of interconnected crowns (undulating rings).

Loops 28 can be the same thickness and profile of the rest of struts 22 or they can be fabricated from a wider (different profile) or thicker/more rigid material to provide torsional rigidity thus preventing rotation of anchor 18 when driven into the tissue/graft.

The configuration of struts 22 of this embodiment of expandable frame 12 can form two rows of offset openings 30 (12 total). Struts 22 can be 0.25-0.6 mm in thickness and 0.2-1 mm in width with a square or round profile and can be fabricated from Nitinol, Chromium-Cobalt or Stainless steel using well known approaches.

Since the length of an expandable frame is related to frame diameter, i.e., collapsing of a frame will increase frame length, the present device can employ strut/ring configurations that eliminate or minimize variations in length between the collapsed and expanded configurations.

Expandable frame can be cylindrical, conical or (half) hourglass in shape with the anchors located anywhere along the length. For example in an hourglass-shaped frame the anchors can be mounted over the distal or proximal crown tips or in the middle section where the frame diameter is the smallest.

When used to anchor a stent graft within an artery, expandable frame can be 5-50 mm in height, 3-5 mm in diameter (collapsed) and 18-38 mm in diameter (expanded). For other applications the length of the expandable frame can be at least 2 (e.g., 2-4) times the diameter.

Proximal end 14 of frame 12 includes eyelets 32 (six shown in FIGS. 1A-3) for facilitating delivery of device 10 into a biological vessel (further described hereinbelow).

Any number of anchors 18 (e.g., 2, 3, 4, 5, 6, 7, 8) can be included in device 10. Each anchor 18 is attached to a distal loop 36 of frame 12 through a tab 37 or frame 38 (frame shown in FIGS. 1A and 2).

Figure 8:
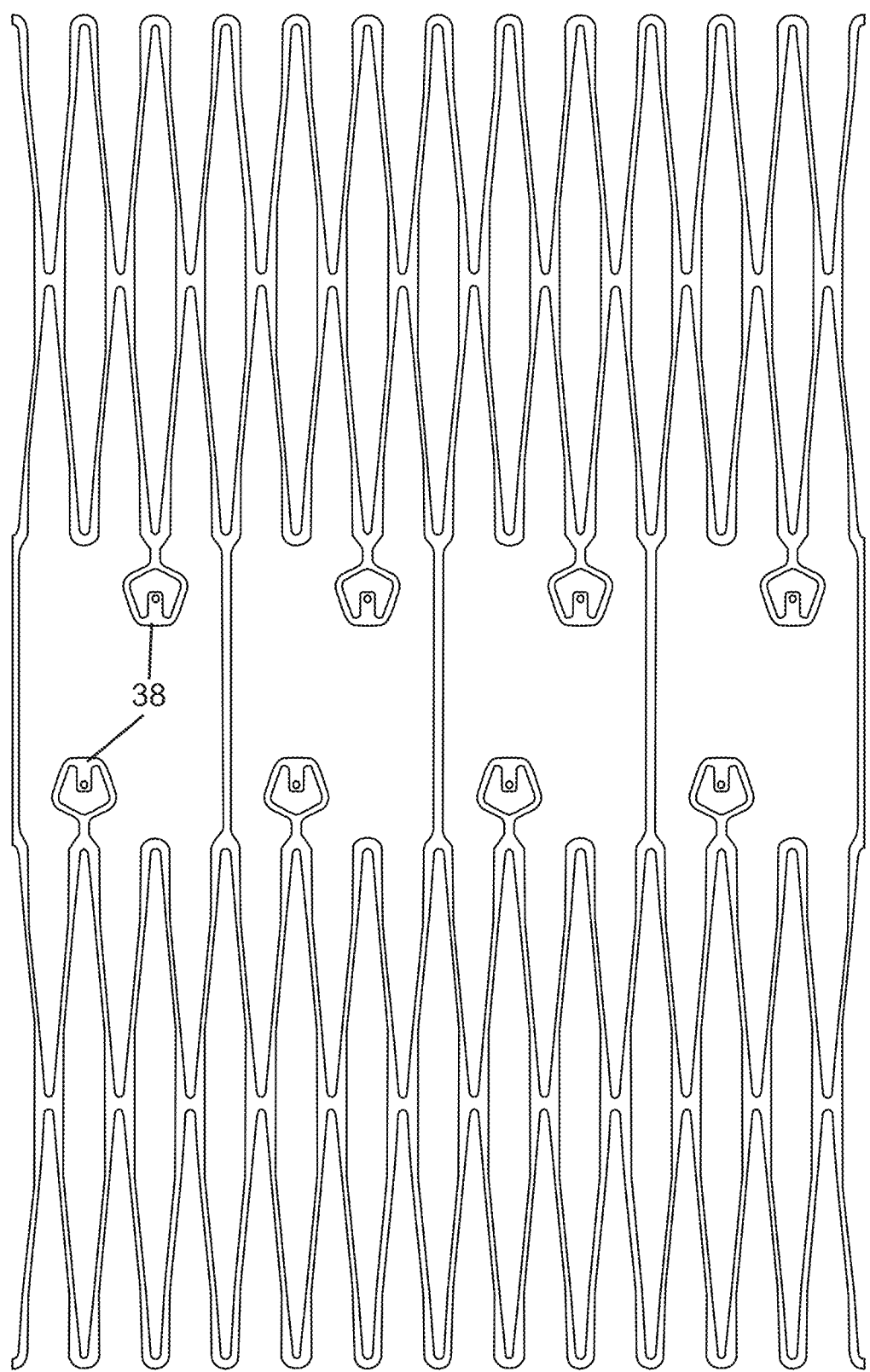
FIG. 8 illustrates a device with a staggered 4×4 anchor configuration.

One example of an anchor 18 configuration is shown in FIG. 8. Such a configuration is advantageous in that it maximizes the number of anchors per delivery diameter. Due to diameter constrains on delivery into a blood vessel, the number of anchors that can be packed within the device is limited. By staggering the anchors (as is shown in FIG. 8), the number of support frames 38 per device can be nearly doubled.

Anchor 18 is shown in more detail in FIGS. 4-6. Anchor 18 includes an anchor body 40 having a base 42 and a tissue penetrating portion 20. Anchor 18 further includes a restraining element 45 for restraining prongs 56 of tissue penetrating portion 20 (further described hereinbelow). Base 42 is attached to frame 38 (FIGS. 4 and 5) or tab 37 (FIG. 6). Base 42 includes an opening 41 through which an extension of tab 37 or frame 38 is attached. Frame 38 or tab 37 are in turn attached to distal loop 36 of frame 12.

Figure 1B:
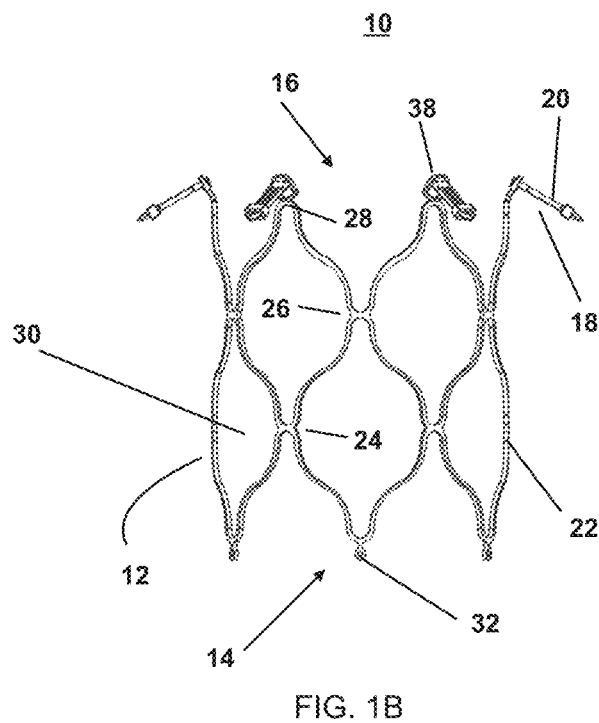
Figure 2:
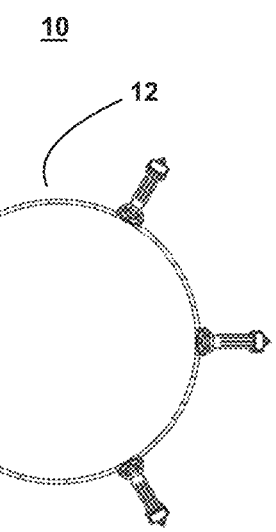
FIG. 2 is a top view of the device of FIGS. 1A-B.
Figure 3:
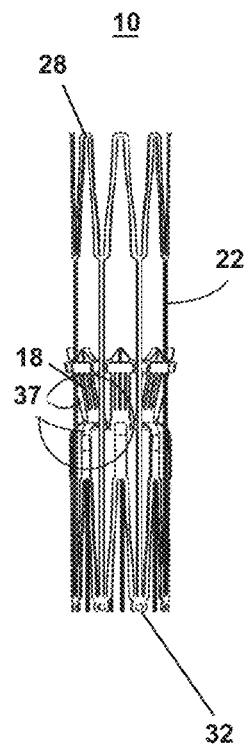
FIG. 3 illustrates an embodiment of the present device in a collapsed (delivery) configuration.
Figure 4:
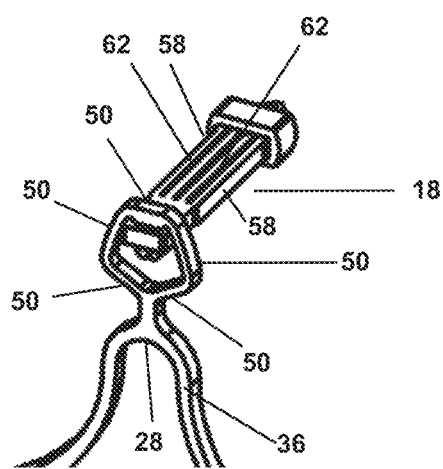
FIG. 4 illustrates an embodiment of the tissue anchor connected through a frame to a strut of the expandable frame of the present device.

Tab 37 and frame 38 function in allowing anchor 18 to elastically bend from a position in which penetrating portion 44 is pointed radially outward (FIGS. 1A-B and 4-5) at 90 degrees (FIGS. 4-5) or less (e.g., 30-60 degrees) as is shown in FIGS. 1A-B to a position in which penetrating portion 44 is pointed about parallel to a longitudinal axis of device 10 (FIGS. 3 and 6).

Tab 37 can be 3-6 mm in length, 0.5-2 mm in width and 0.2-0.5 mm in thickness. Such a tab fabricated from Nitinol can have a modulus of elasticity sufficient to allow bending through 90 degrees or more.

Frame 38 can include 3, 4, 5, 6 beams 50 (5 shown in FIGS. 4 and 4 shown in FIG. 5). Beams 50 distribute the bending stress and may enable a larger range of bending (90-120 degrees). Tab 37 and frame 38 can be manufactured from the same tube. If the tube wall thickness is high (for example over about 0.25 mm) the strain on tab 37 will exceed the desired limit. This can be solved by fabricating a longer tab 37 (which would limit delivery diameter) or by mounting anchor 18 on a frame 38 which allow the required 90-120 degree bending while keeping the construction material within the supper-elastic range. Beams 50 can be 0.5-2 mm in length, 0.2-1 mm in width and 0.2-0.6 mm in thickness.

As is shown in FIG. 5, beams 50 provide both bending (beams 52) and torsion (beams 54) and thus distribute the stresses (strain) applied to frame 38.

In order to crimp the device into a 16-18 French (fr) delivery catheter and enable release of the anchors from parallel to angled (e.g., a range of bending of 90-120 degrees), the maximum strain should be kept bellow 7-8% (Nitinol) in any section of the support frame. Given that the required strain for the anchored crimping is K, once that strain is divided between the beams (bending strain and torsional strain) the maximum strain can be kept under the above strain limitation.

A tab can also meet the above 7-8% strain requirement but in order to do that it should be very thin and relatively long which will make it less resistant to twisting during anchor delivery into graft and tissue.

Anchor 18 can be attached to frame 38 internally (FIG. 4) or externally (FIG. 5). External location of anchor 18 will result in a more internal position when device 10 is collapsed.

Figure 7:
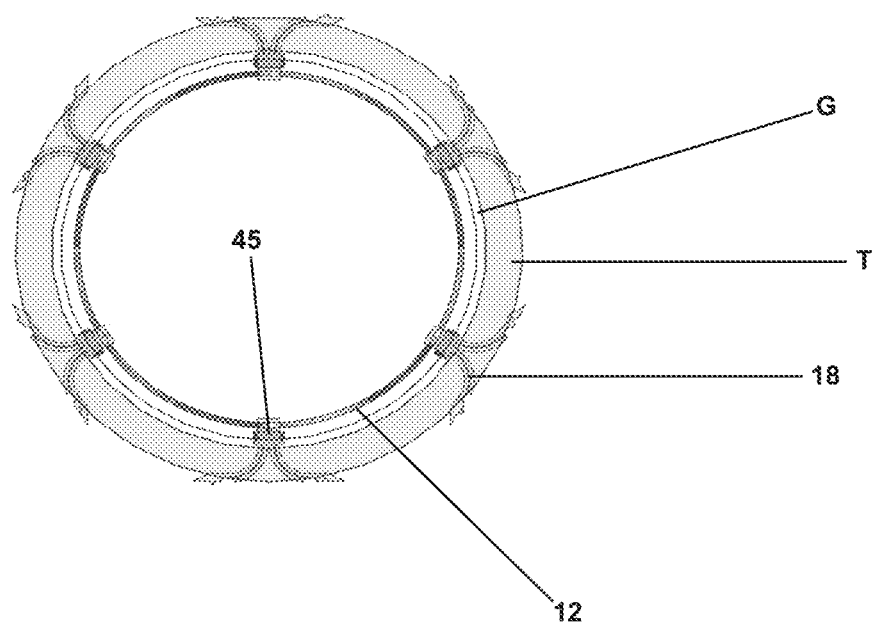
FIG. 7 illustrates the tissue anchor with the two prongs of the tissue penetrating portion splayed out.

In the embodiment shown in the Figures, tissue penetrating portion 20 of anchor 18 includes 4 prongs 56, two external prongs 58 having tissue penetrating tips 60 and two internal prongs 62 for facilitating splaying out of tissue penetrating portion 20 (FIG. 5). Anchor 18 applies an anchoring (stapling) force between the graft and the tissue that is strongly correlated (^3) to the prong width. The pre-shaped anchor 18 (open state) is restrained to a straight arrow shape during delivery but is designed to return to the initial (splayed) shape following penetration through graft (G) and/or tissue (T) as is shown in FIG. 7. In order to achieve such functionality, the maximum strain of prongs 56 should not exceed 7-8%. Thus, in order to achieve the clamping forces without significantly changing the dimensions of anchor 18 and its elasticity, prongs 56 are doubled (i.e., 2 prongs per side for a 2× clamping force).

The penetrating tips (two, one for each external prong) can be arrow-shaped (30-90 degrees) and beveled at 90-130 degrees. The arrow shape of the tip can be created by laser cutting of a Nitinol sheet and the bevel can be created via grinding. Each prong 56 can be separately cut and then joined to make anchor 18.

Restraining element 45 (e.g., sleeve/collar) is fitted over tissue penetrating portion 20 and can slide between tips 60 and base 42. Tips 60 can include a stop 64 for preventing restraining element 45 from sliding off of tissue penetrating portion 20.

When tissue penetrating portion 20 is pushed into tissue/graft, restraining element 45 slides backwards (forced backwards by the tissue/graft) to release restraint of prongs 56. When released, prongs 56 splay outward (open) to the position shown in FIG. 7. This enable tissue anchor 18 to anchor against the far side of the tissue/graft. Prongs 56 of anchor 18 are pre-shaped in the configuration shown in FIG. 7 are constrained in the linear configuration shown in, for example, FIG. 5 by fitting restraining element 45 over tissue penetrating portion 20 near the tip.

As is mentioned hereinabove, device 10 of the present invention can be used to anchor a stent-graft during or following an aortic aneurysm repair procedure.

A delivery system 100 (also referred to herein as "delivery catheter 100") and a balloon catheter 200 suitable for use in delivering and deploying device 10 in the vasculature are illustrated in FIGS. 9A-H and FIG. 10 (respectively).

The present device is delivered and released at a target location by using a 16-18 fr compatible, 600-800 mm working length delivery catheter 100 (FIGS. 9A-G). A 14-18 fr compatible, 600-800 mm working length balloon catheter 200 (FIG. 10) can be inserted through the delivery system to lock and activate the device or it can be independently delivered over the wire following removal of the delivery system.

Figure 9A:
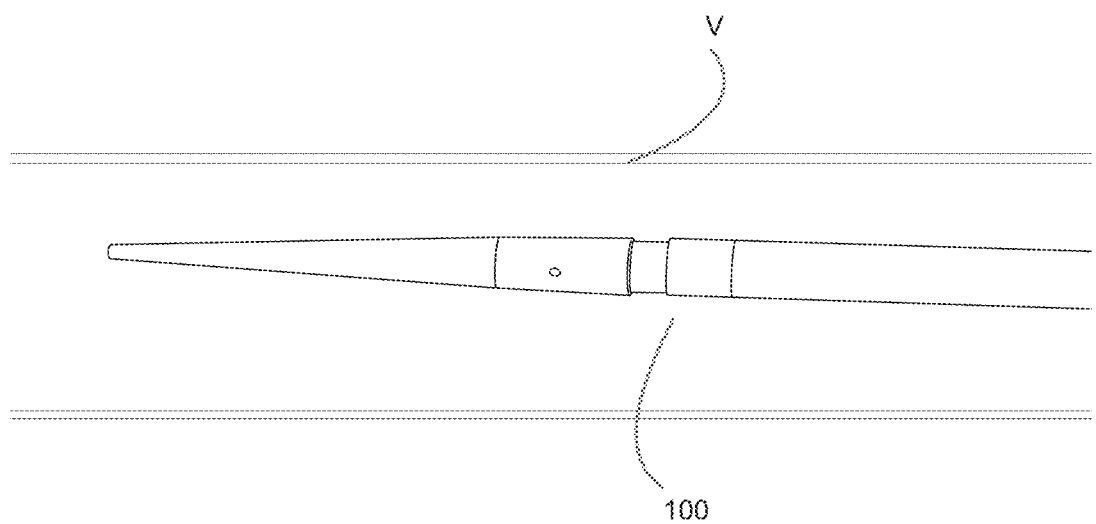
FIGS. 9A-H illustrate delivery of the present device into a blood vessel and the delivery apparatus used for positioning the device in the vasculature.
Figure 9B:
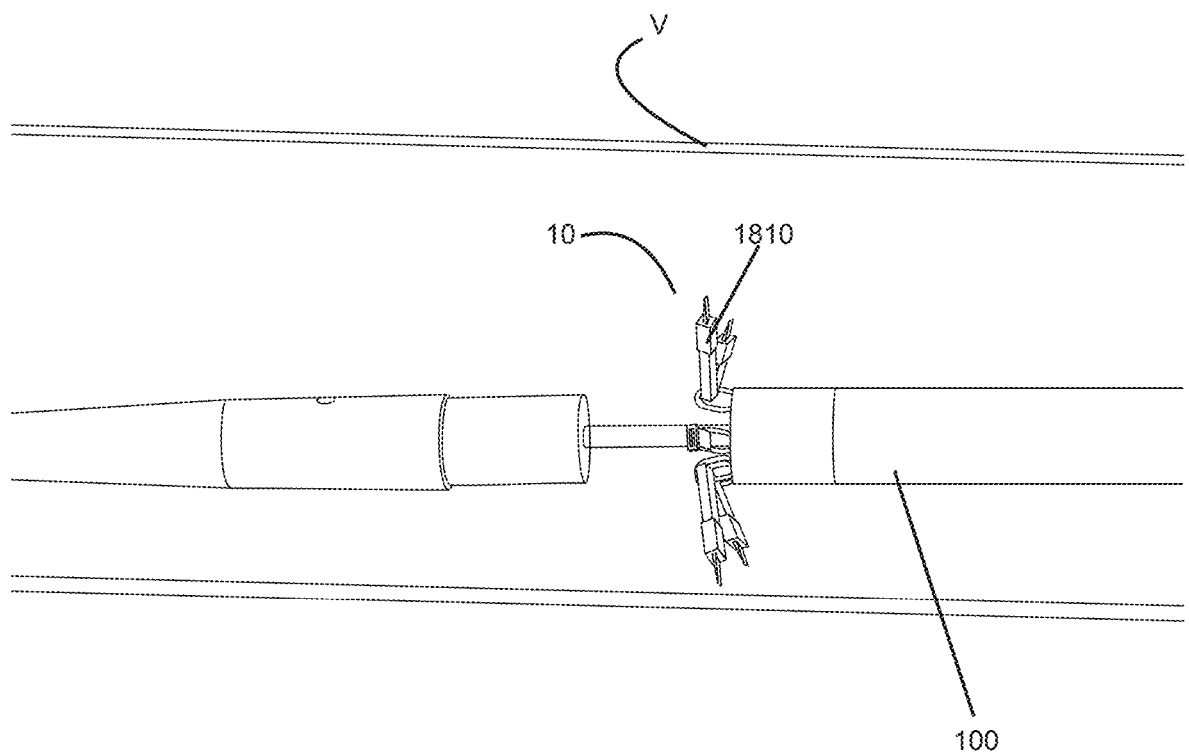
Figure 9C:
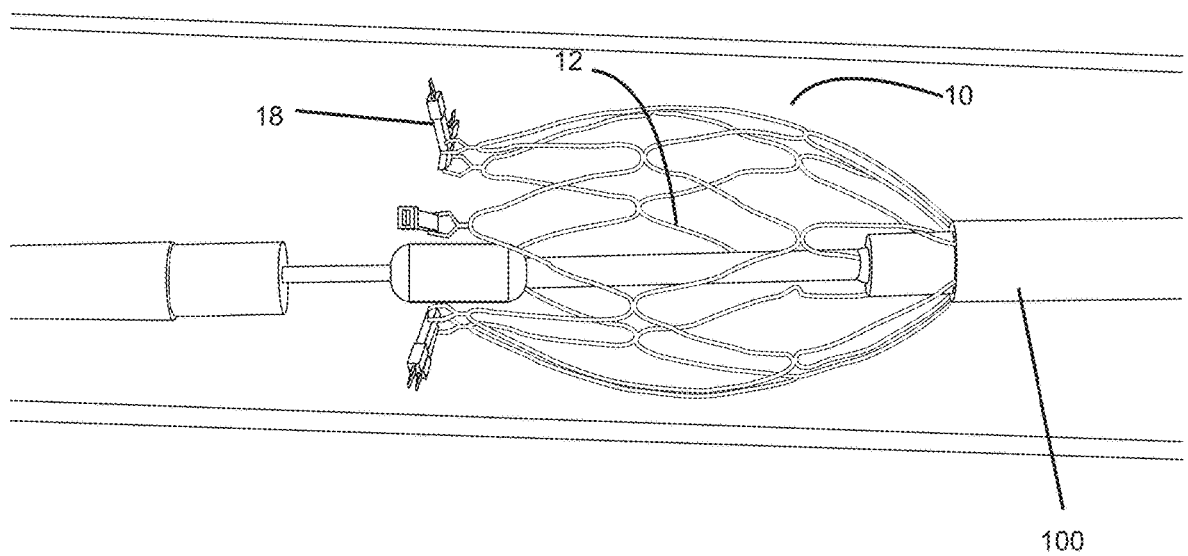
Figure 9D:
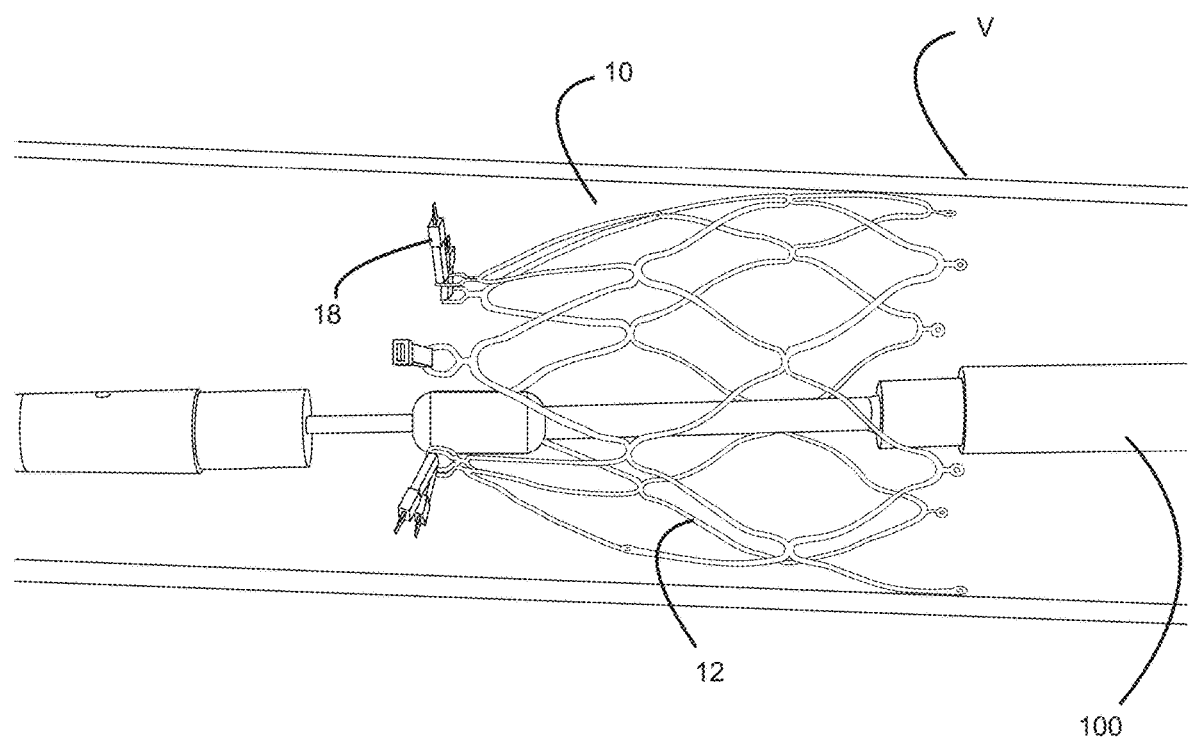
Figure 9E:
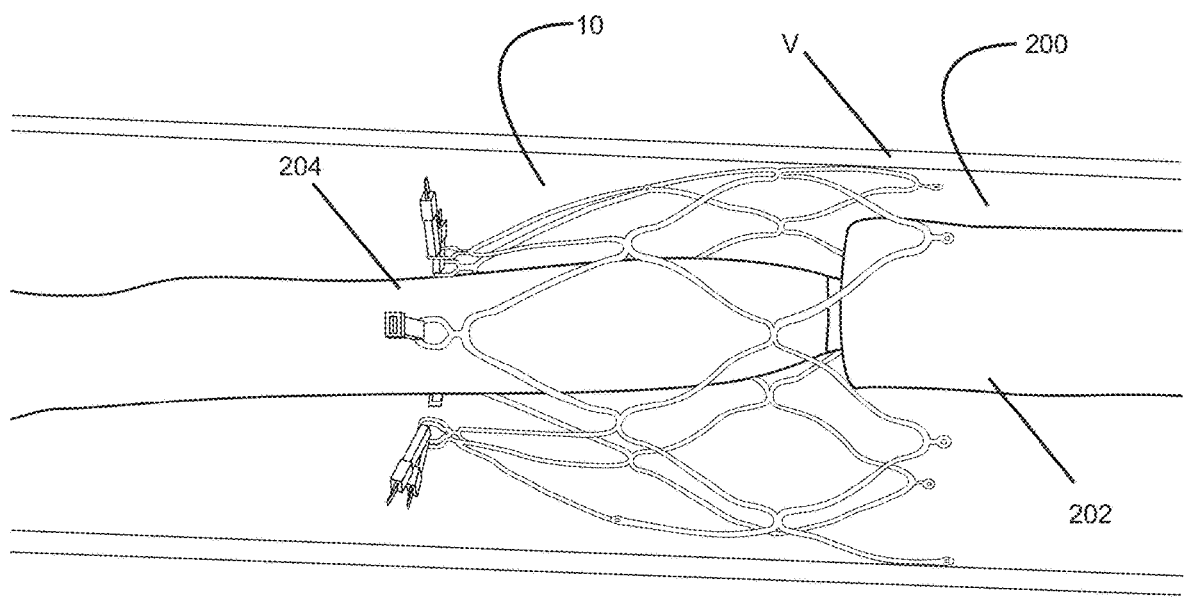
Figure 9F:
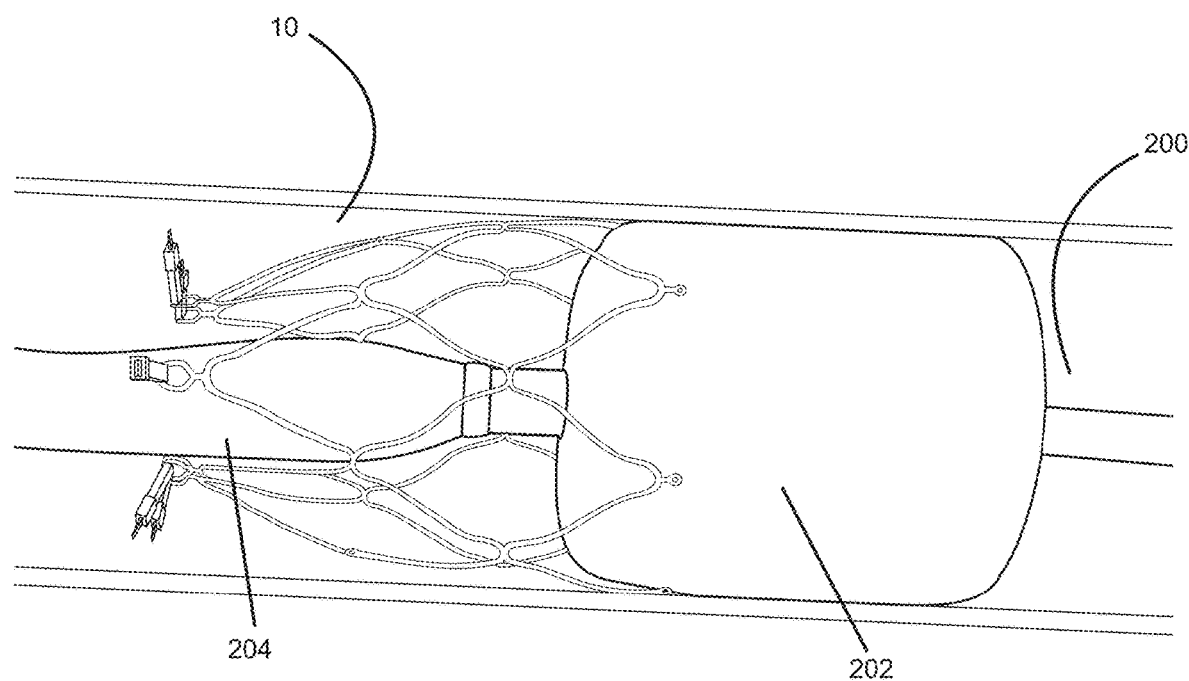
Figure 9G:
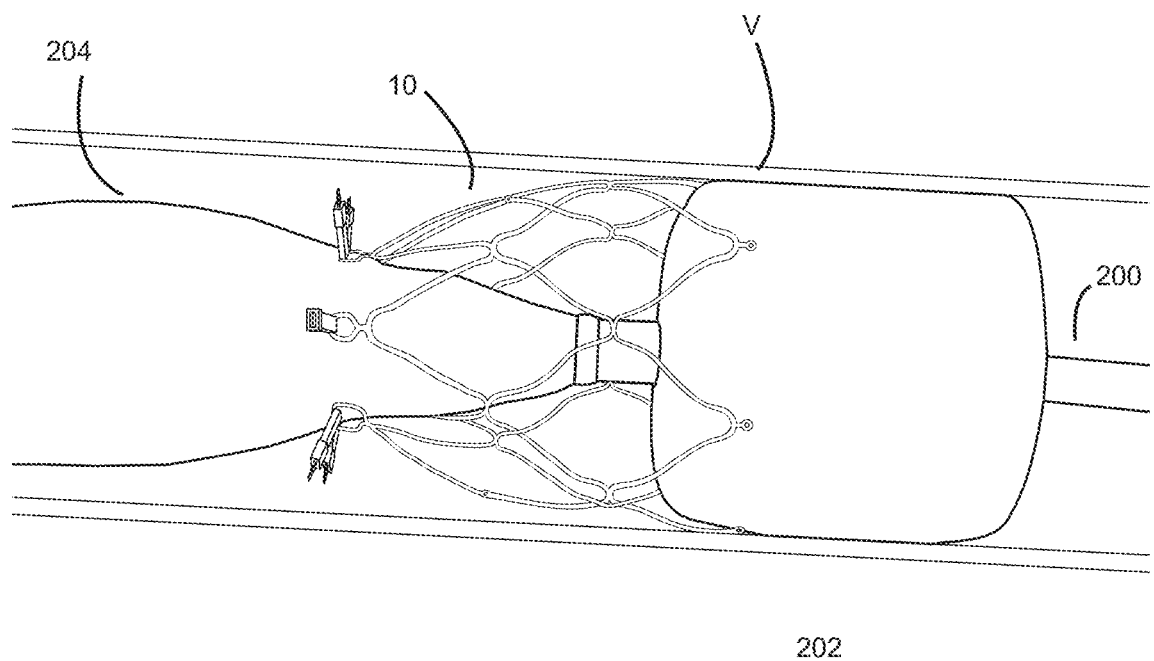
Figure 9H:
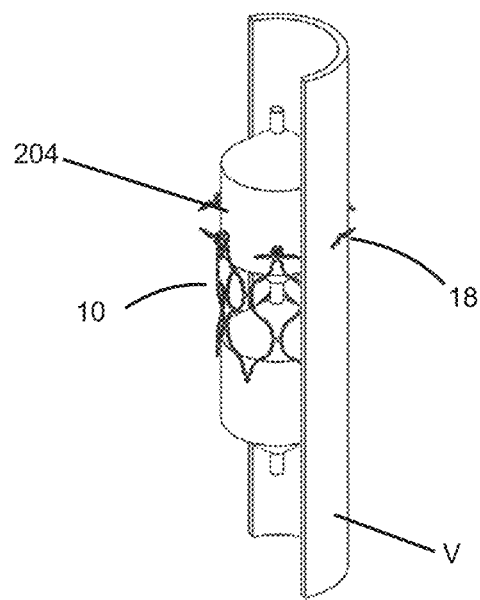

Delivery of the device is effected as follows, delivery catheter 100 is advanced over a wire through the vasculature (V) from an access site (e.g., femoral) to a deployment target. Device 10 is partially unsheathed Proximally (FIG. 9A) and distally (FIG. 9B) to deploy anchors 18 outward. Device 10 is further unsheathed to deploy the expandable frame (FIG. 9C) and release the device from catheter 100 (FIG. 9D). In the procedure shown in FIGS. 9A-G, delivery catheter 100 is then be retracted from the body over the wire. A dual balloon catheter 200 is then advanced over the wire and balloons 202 and 204 of catheter 200 are positioned within device 10 (FIG. 9E). Radiopaque markers on balloon catheter 200 shaft enable accurate positioning of balloons 202 and 204. Proximal balloon 202 (nylon, Pbax, Polyurethane, length 10-15 mm) is then inflated to 0.5-1 atm and a diameter of 25-40 mm to lock the proximal end of device 10 (expandable frame 12) against the graft or tissue while radially centering distal balloon 204 at anchors 18 (FIG. 9F). Distal balloon 204 (nylon, Pbax, Polyurethane, length 10-15 mm) is then inflated to 1-4 atm and a diameter of 20-35 mm to force anchors 18 through the graft and aortic wall and effectively staple the graft to the tissue (FIGS. 9G-H).

Figure 10:
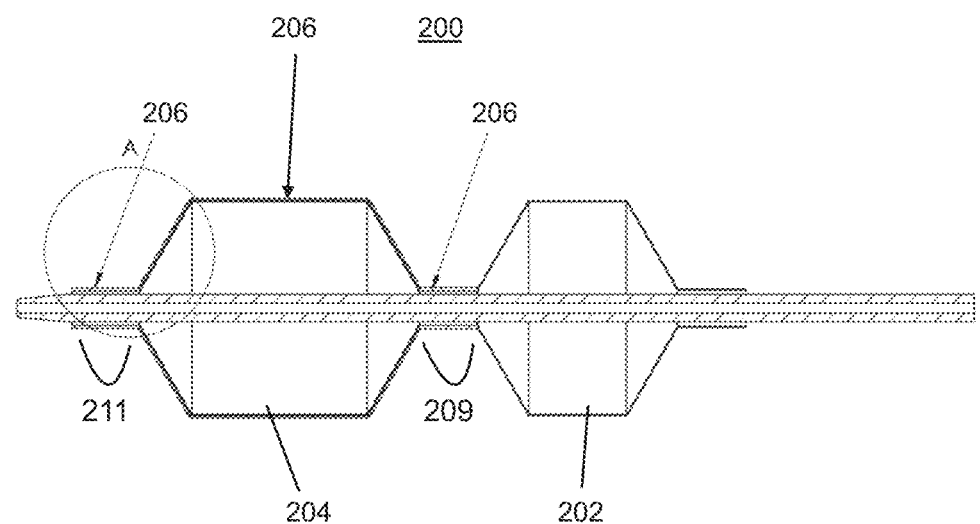
FIG. 10 illustrates a balloon catheter for anchoring the present device to the tissue and graft.

As is shown in FIG. 10, distal balloon 204 (semi-compliant or compliant) can be covered by a compliant sleeve 206 (0.1-0.4 mm thick, TPU, Silicon, Latex etc.) that can serve to protect distal balloon 204 from being punctured by the base/frame/tab of anchor 18 during inflation. Sleeve 206 can be glued/bonded/welded along necks 209 and 211 (circumferentially) to balloon 204. When deflated, balloon 204 can be folded within sleeve 206 as is shown in FIG. 13C.

Figure 13A:
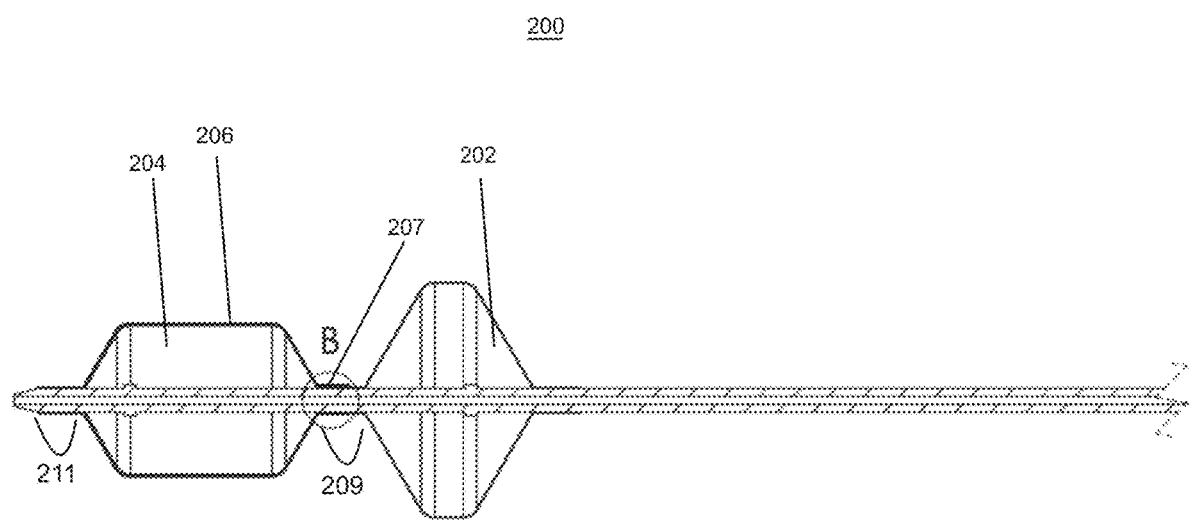
FIGS. 13A-C illustrate the balloon catheter of FIG. 10 (FIG. 13A) showing the region forming the opening between the sleeve and distal balloon (magnified in FIG. 13B) and the arrangement of the deflated and folded distal balloon and sleeve (FIG. 13C).
Figure 13B:
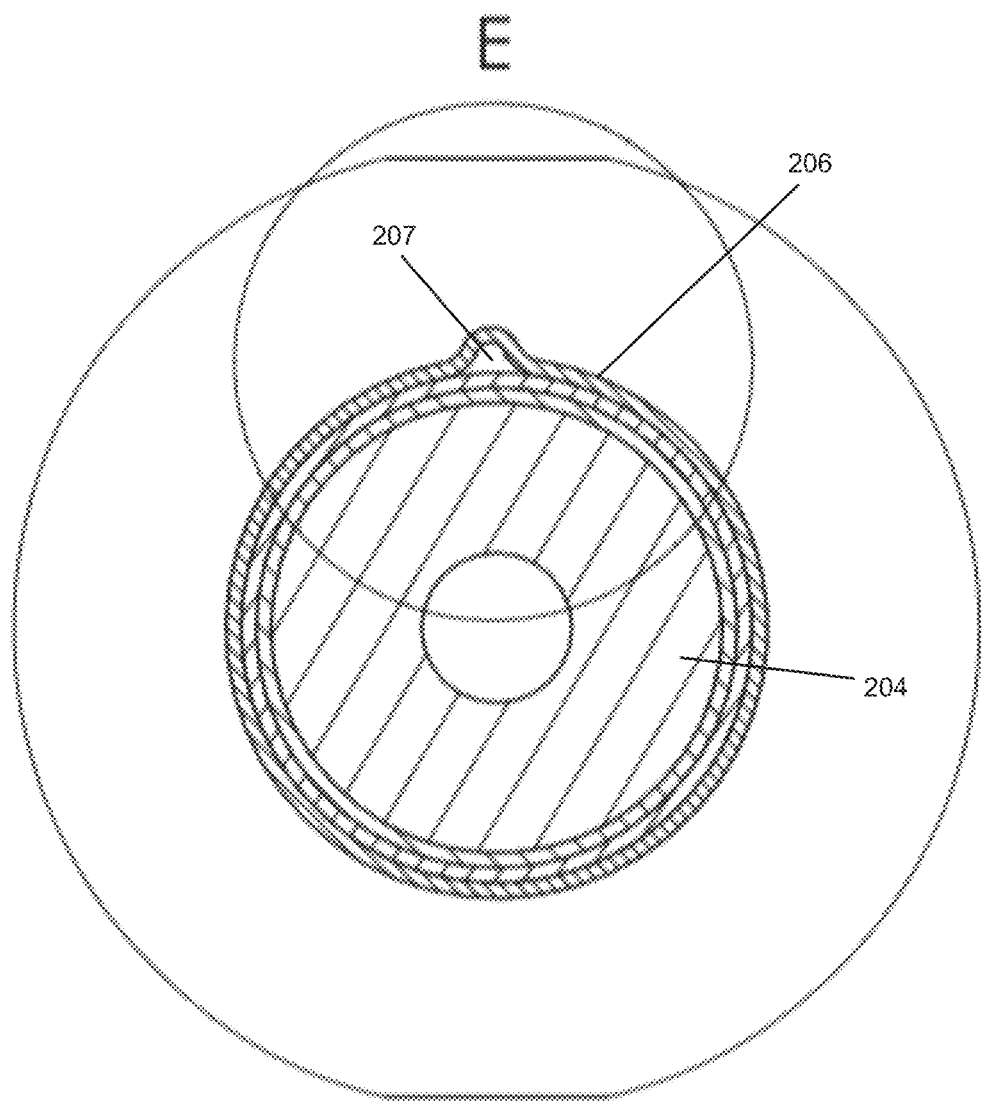
Figure 13C:
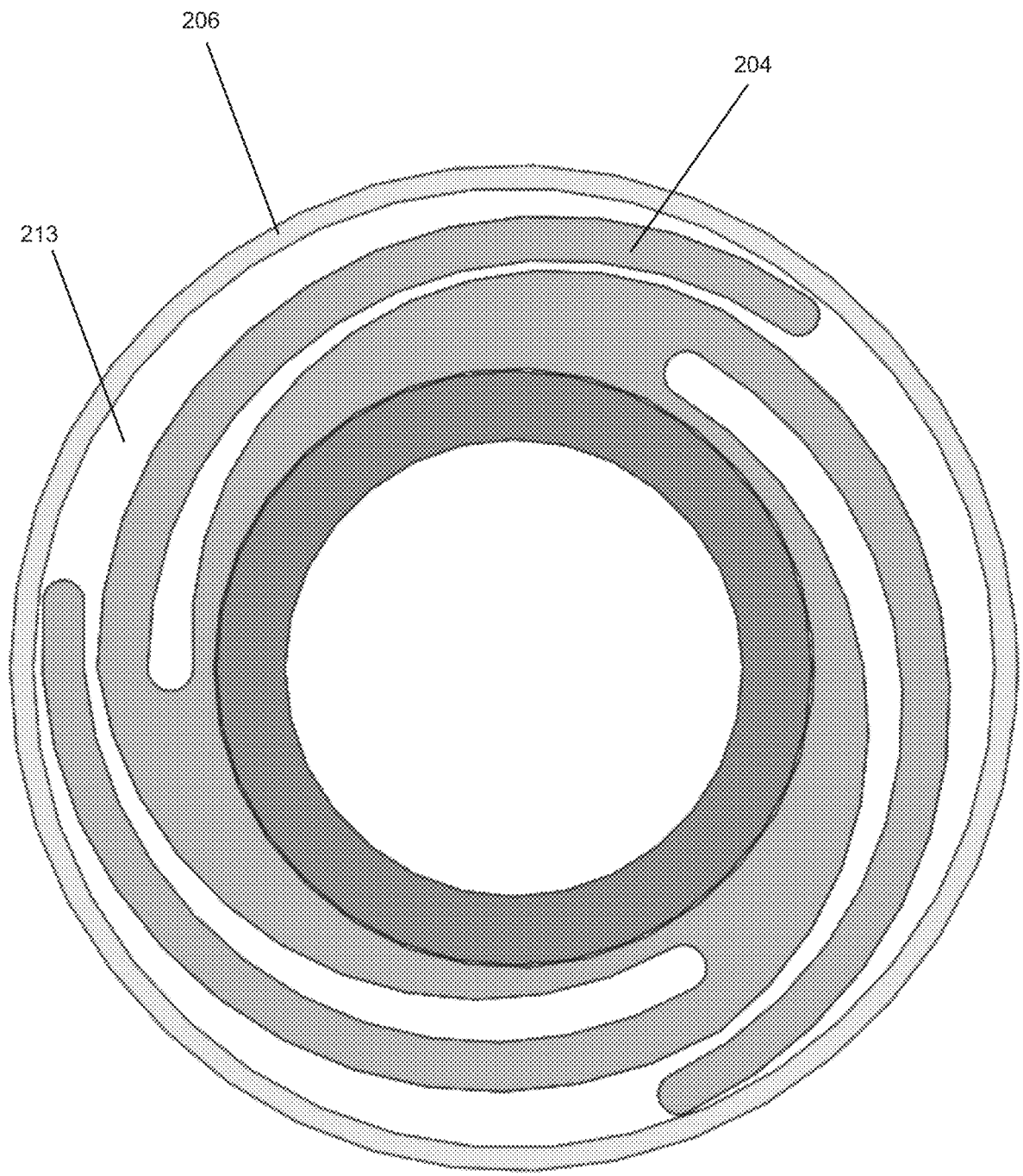

As is shown in FIGS. 13A-B, balloon catheter 200 can also include a conduit 207 running along neck 209 and/or 211 between balloon 204 and sleeve 206. Conduit 207 can be formed by not gluing/bonding/welding balloon 204 to sleeve 206 along a 5-15 degree circumferential arc of neck 209 and/or 211. Conduit 207 allows air trapped between balloon 204 and sleeve 206 to be evacuated using a priming procedure prior to use of balloon catheter 200. If air trapped between a folded balloon 204 and sleeve is not evacuated, sleeve 206 can rupture and release air bubbles into the blood stream. Conduit 207 allows a user to prime (deair) balloon catheter 200 outside the body by inflating balloon 204 and deflating it in a liquid (e.g., saline solution). Once balloon catheter is primed it can be inserted into the body to deliver device 10.

Conduit 207 also allows sterilization of a gap 213 (FIG. 13C) between balloon 204 and sleeve 206 by flowing a sterilization gas (ETO) into gap 213 through conduit 207.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non-limiting fashion.

Porcine Model

Figure 11:
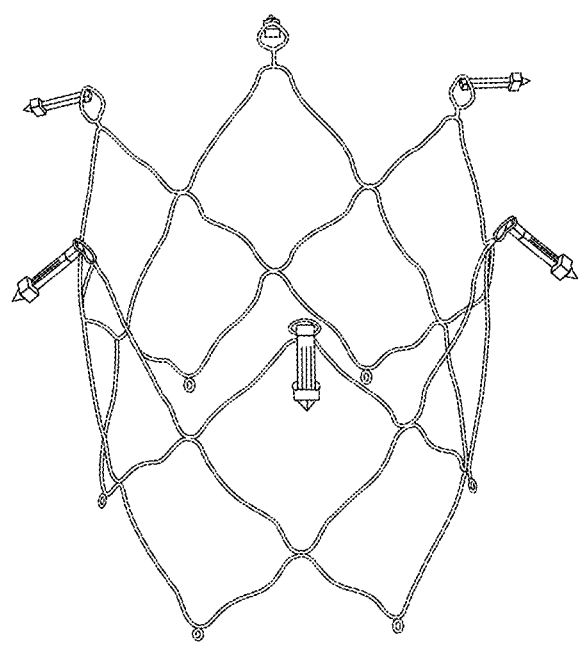
FIG. 11 is a prototype of the present device.
Figure 12:
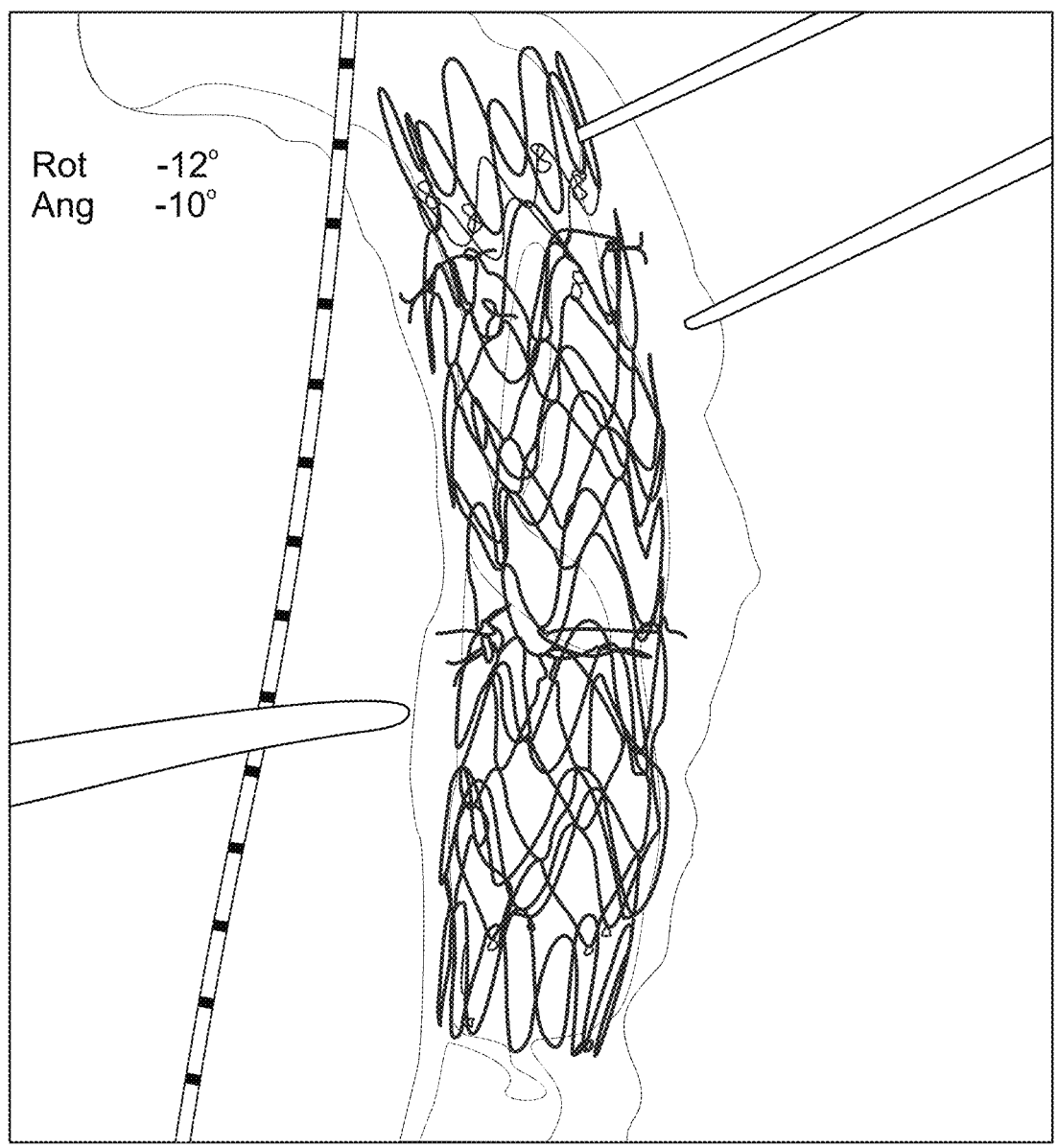
FIG. 12 is an angiogram showing the present device anchored in a section of a porcine aorta.

A pig model was used to test anchoring of a graft to a porcine aorta using two tissue anchoring devices (FIG. 11). A 120-130 Kg female pig was anesthetized and an 18-20fr introducer catheter was introduced over the wire via femoral access. A graft was implanted in the descending aorta using a standard procedure and a first device was delivered, located and released within the graft using the dedicated delivery system described hereinabove. The delivery system was retracted and a dual balloon catheter was inserted (over the wire) and located using dedicated imaging markers such that the proximal balloon overlapped the proximal end of the device frame. The proximal balloon was inflated to 1 atm to lock the frame against the graft and aorta wall and center the distal balloon. The distal balloon was then inflated to 2-2.5 atm to drive the anchors through the graft and aortic wall, imaging was used to confirm anchor penetration and deployment. The balloon catheter was deflated and retracted and the process was repeated for a second device positioned proximally to the first device. The pig was sacrificed and an aortic section was excised and examined under X-ray to verify graft to aorta anchoring (FIG. 12).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

In addition, any priority document(s) of this application is/are hereby incorporated herein by reference in its/their entirety.

What is claimed is:

1. A tissue anchoring device comprising an expandable frame having a proximal end and a distal end and at least one anchor having a tissue penetrating portion attached to said expandable frame through a support frame including a first beam and at least one second beam being indirectly attached to said expandable frame, said at least one anchor is capable of elastically bending with respect to a longitudinal axis of said expandable frame through torsion of said first beam and bending of said at least one second beam of said support frame, wherein said tissue penetrating portion includes two tissue-penetrating prongs and a restraining element for restraining said two tissue-penetrating prongs in a parallel configuration for co-delivery into a tissue and for releasing said two tissue-penetrating prongs to splay out away from each other following penetration through said tissue and resulting backward movement of said restraining element along said two tissue-penetrating prongs.

2. The device of claim 1, wherein said support frame is shaped as a pentagon.

3. The device of claim 1, wherein said tissue penetrating portion of said at least one anchor is pointed at an angle of 45-70 degrees with respect to a longitudinal axis of said expandable frame.

4. The device of claim 3, wherein said at least one anchor can be elastically bent from a first direction in which said tissue penetrating portion points at said angle to a second direction in which said tissue penetrating portion is generally pointing parallel to said longitudinal axis of said frame.

5. The device of claim 1, wherein said restraining element is a restraining sleeve.

6. The device of claim 5, wherein said tissue penetrating portion includes a stop for preventing movement of said restraining sleeve over a tissue penetrating tip of said tissue penetrating portion.

* * * * *